US012693730B2

(12) United States Patent
Hammerberg et al.

(10) Patent No.: US 12,693,730 B2
(45) Date of Patent: Jul. 28, 2026

(54) SYSTEM AND METHOD FOR MOVEMENT DATA ANALYSIS AND MONITORING

(71) Applicant: HOMININ.AI INC., Seattle, WA (US)

(72) Inventors: Alexandra Hammerberg, London (GB); Brandon Taft, London (GB); Marcus Bowyer, Seattle, WA (US); Samuel Grunblatt, Baltimore, MD (US); Howard Lee, Seattle, WA (US)

(73) Assignee: HOMININ.AI INC., Seattle, WA (US)

( * ) Notice: Subject to any disclaimer, the term of this patent is extended or adjusted under 35 U.S.C. 154(b) by 0 days.

(21) Appl. No.: 19/019,204

(22) Filed: Jan. 13, 2025

(65) Prior Publication Data

US 2025/0231612 A1 Jul. 17, 2025

Related U.S. Application Data

(60) Provisional application No. 63/620,736, filed on Jan. 12, 2024.

(51) Int. Cl.
*G06F 3/01* (2006.01)
*A61B 5/11* (2006.01)

(52) U.S. Cl.
CPC ............ *G06F 3/011* (2013.01); *A61B 5/1118* (2013.01)

(58) Field of Classification Search
None
See application file for complete search history.

(56) References Cited

U.S. PATENT DOCUMENTS

2024/0207682 A1* 6/2024 Matsimanis ........... G06N 5/022

* cited by examiner

*Primary Examiner* — Aneeta Yodichkas
(74) *Attorney, Agent, or Firm* — Krista A. Wittman

(57) ABSTRACT

A method for biomechanical data analysis and monitoring is provided. Movement data is collected from one or more wearable devices associated with a user. Environmental data is integrated with the movement data by correlating the environmental data with specific points of the movement data. A power spectral profile is built for the user based on the movement data and environmental data, and includes a movement profile for the user. The power spectra is correlated with environmental factors and with data reported by the user. Variations of the power spectral profile are provided based on the environmental factors.

10 Claims, 4 Drawing Sheets

10

<u>30</u>

40

60

SYSTEM AND METHOD FOR MOVEMENT DATA ANALYSIS AND MONITORING

FIELD

This invention relates in general, to collecting data for activity and health projections and in particular, to a system and method for movement data analysis and monitoring.

BACKGROUND

The use of consumer wearable devices, such smart phones, smart wrist devices, and headphones has quickly increased to a level where a majority of adults in the U.S. are associated with at least one device. Smart phones include sensors to collect user data and provide users with call access, Internet, Bluetooth, messaging, and other features. Similarly, smart watches, hearing aids, and headphones, such as earbuds or over the ear headphones, also track user data. The user data can include movement metrics of a user, such as steps, runs, acceleration, location, distance, pace, and other metrics.

Every individual moves differently and can be associated with a personal baseline of movement metrics to compare with later collected metrics. For example, many individuals track their step count daily to ensure that they meet their step requirement for the day. Days of heavy activity, such as walking around Disneyland or going on a longer-than-normal run, generally result in higher step counts than lighter activity days. Also, runners often track distance and pace for every run, which they can compare day-by-day or run-by-run to determine whether they are increasing pace and distance over time.

The collection and tracking of movement metrics encourages individuals to be active by reporting daily metrics, milestones, achievements, and progress. However, based only on the conventional movement metrics, there is a limit as to what information is provided to the individual. The ability to determine and provide additional information to individuals will help provide a more detailed analysis to the user with respect to her movement metrics. For example, movement-based biomarkers, such as subtle changes to an individual's walking mechanics, can be used to identify early indicators of musculoskeletal or neurological disease or injury, predict exacerbations in health conditions allowing early intervention, and optimize recovery from injury.

Further, although individual movement metric data is available, some companies are currently training movement models on aggregate sets of human data to make assumptions at a population level. The models are then applied to "everyone," which results in broad generalizations that can be inaccurate for many based on personal features or characteristics not considered by the aggregate approach. Thus, such an aggregate approach fails to accurately predict injury and identify milestones on an individual level. For example, while the gross pattern of bipedal locomotion is consistent across humans (i.e. propulsion and braking on alternating legs via an oscillating stance and swing phase), the details of each individual's movement patterns and mechanics are unique, as are the details of their mechanical adaptations to environmental conditions, such as terrain changes. This uniqueness presents a challenge to identifying movement-based biomarkers of pathologies or deviations from "normal" that may indicate changes to health. "Normal" is an individual baseline that is the key to personal health monitoring outside of the clinic and to early intervention.

Therefore, a need remains for generating accurate and detailed individual movement profiles and providing population-level analyses based on the individualized profiles. Preferably, the profiles are based on movement metrics and environmental data not previously considered. Additionally, the individual profiles can be used to provide population-level analysis for information regarding group behavior and health data.

SUMMARY

Movement data collected for a user can be used to generate a movement profile, which describes how that user is moving in space. The individualized movement profile can be used or correlated with other data to predict injury or inform of behavior and health issues. Further, the individual profiles can be aggregated and used as training data for population level models to provide analysis on behavior and health for a population based on location, such as neighborhood, city, or state.

An embodiment provides a method for biomechanical data analysis and monitoring. Movement data is collected from one or more wearable devices associated with a user. Environmental data is integrated with the movement data by correlating the environmental data with specific points of the movement data. A power spectral profile is built for the user based on the movement data and environmental data, and includes a movement profile for the user. The power spectral profile is correlated with environmental factors and with data reported by the user. Variations of the power spectral profile are provided based on the environmental factors.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Collecting data, such as movement metrics, of an individual is helpful to track daily movement and progress. For example, a runner can track steps, distance, time, and pace over time to see if one or more of those metrics are improving. However, during some runs, the runner, for example, experiences heel pain. When looking at the movement metrics, the user can only determine that the runs with heel pain correlate, perhaps, with a lesser distance and a slower pace.

Comparing the movement metrics with further information, such as environmental data and external data, such as from the user, would provide additional detailed information that could be used to diagnose, determine, and predict health conditions, causes, and status. For instance, returning to the example above, the run metrics of the user are compared with environmental data, such as running surface type, and a correlation is identified between heel pain and runs occurring on pavement. Such information can be provided to the user to avoid running on pavement to prevent heel pain.

With the rise of movement sensor integration in consumer wearable devices, such as headphones, smartphones, and watches, it is now possible to quantify a movement baseline and monitor movement biomarkers at the individual level. In gait monitoring, the head is an optimal location due to its stable position in relation to the rest of the body, thus, reducing signal noise. Wearable device manufacturers and apps that utilize their data, however, rely on movement models trained towards the population average on aggregate data, lacking environmental context. Creating individual movement models requires the development of a new approach to quantifying human movement, which involves collecting and outputting power spectra profiles, frequency domain models, and individual-level large movement models.

Figure 1:
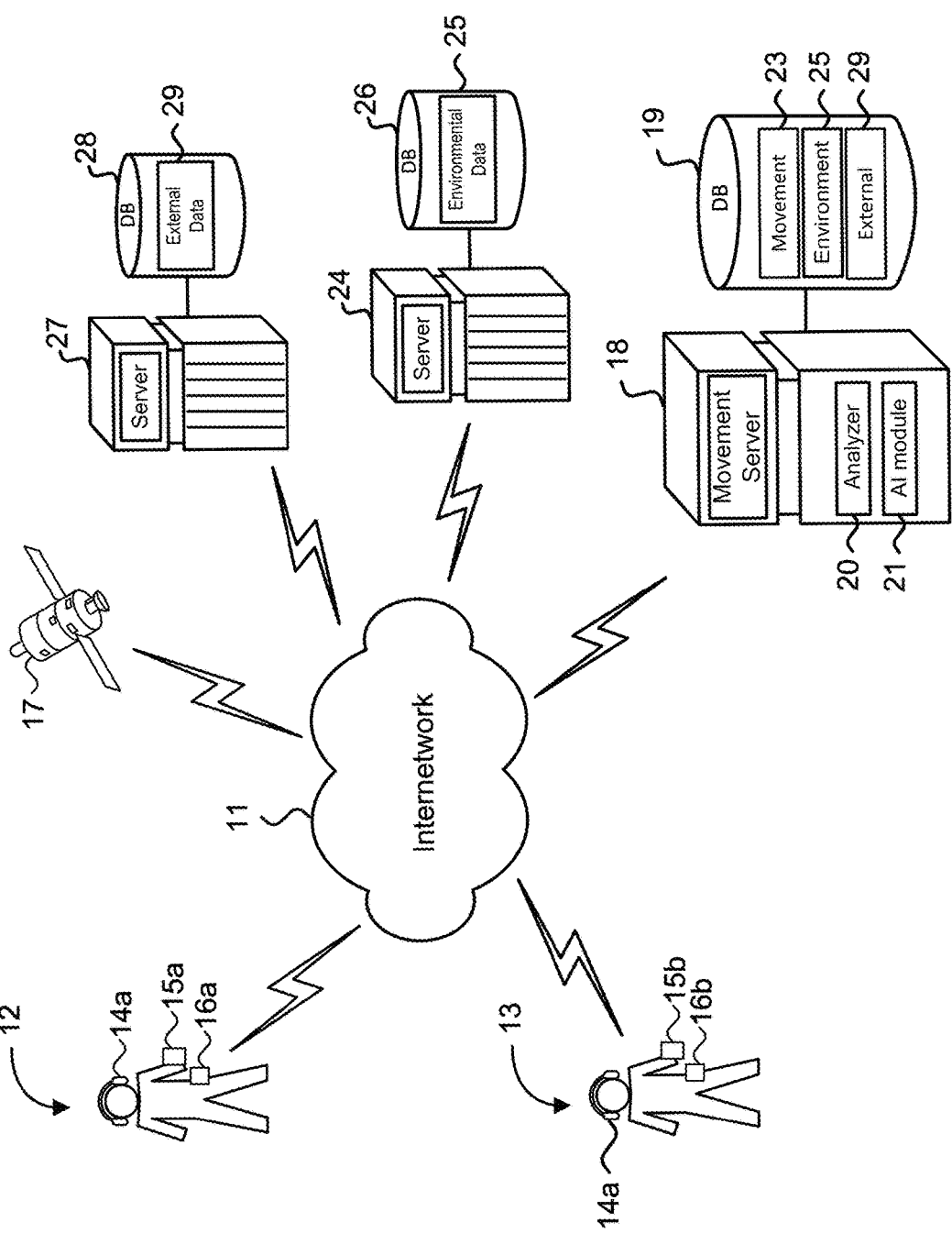
FIG. 1 is a block diagram showing a system for biomechanical data analysis and monitoring, in accordance with one embodiment.

Detailed information obtained from raw signals for movement metrics, environmental data and external data can be aggregated for individuals and used to provide population-level analysis regarding health and behavior. FIG. 1 is a block diagram showing a system for biomechanical data analysis and monitoring, in accordance with one embodiment. Individuals 12, 13 can each wear one or more mobile devices, such as a smart headphone set 14 *a,b*, a smart watch 15 *a,b*, or a cellphone 16 *a,b*, that collects movement data 23, including accelerometer, gyroscope, GPS, altimeter, and barometer data. Other types of wearable mobile devices are possible, such as smart glasses, including Meta glasses. An application running on one of the mobile devices can transmit the movement data 23 to a movement server 18 via an Internetwork 11, such as the Internet, for processing and analysis as well as storage in a database 19 interconnected to the movement server 18. Specifically in one embodiment, an API or SDK is generated to plug into existing applications by third parties to obtain the movement data and in turn, provide advanced information and results based on the movement data.

Figure 2:
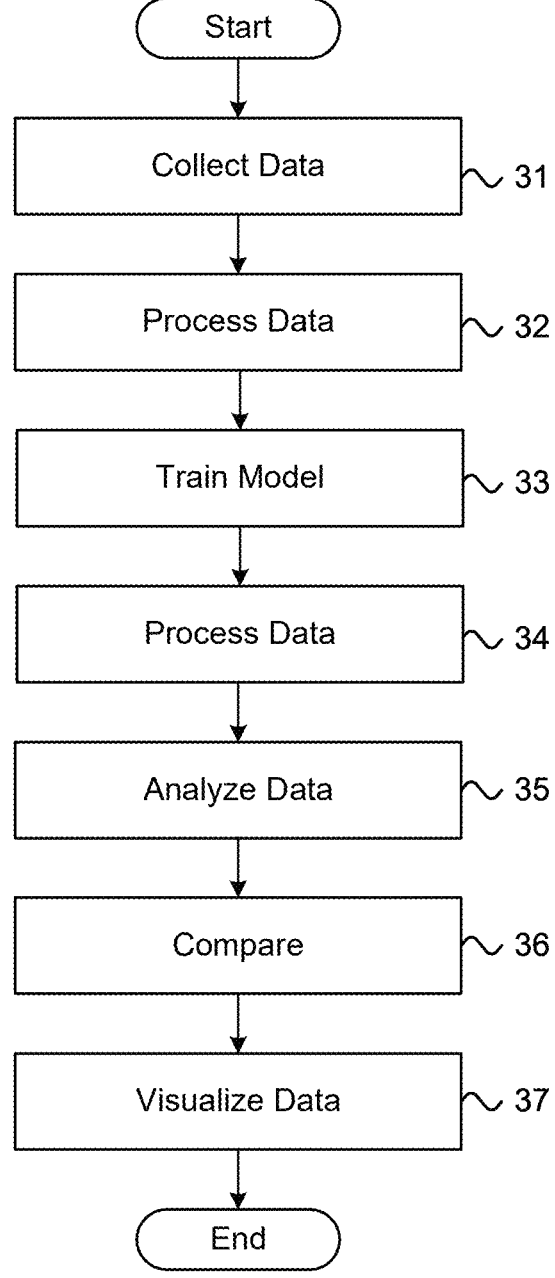
FIG. 2 is a flow diagram showing a method for biomechanical data analysis and monitoring, in accordance with one embodiment.

The server 18 includes an analyzer 20 to process the movement data by preprocessing the data, enriching the data, and finalizing the data, which is further described in detail below, with respect to FIG. 2. During the data enriching step, external data 29 is collected from a database 28 interconnected to one or more servers 27 and environmental data 25 is collected from a database 26 interconnected to one or more servers 24. The external data 29 and environmental data 25 is stored in the database 19 interconnected to the movement server 18 and used with the movement data 23 to provide additional detail about the user's movement patterns. The servers and databases can be part of a cloud computing environment or the servers can be dedicated.

Once processed, the external, environmental, and movement data is provided to an AI module 21, which uses at least a portion of the data as training data for generating and refining a model, such as an individual-level large movement model to recognize and predict injury, health status, or behavior of an individual or for a population of people each associated with an individual-level large movement model. The other portion of the data can be provided to the AI module for analysis using the trained model. Results of the analysis provide detailed movement information on an individualized level or population level and can be returned to the individual for display or provided to a company for review.

As part of the data processing, a power spectra profile is generated for each individual from which data is collected to help make injury or health predictions, calculate values for parameters, and label parameters. Parameters refer to the data collected, as well as data that is determined based on processing of the collected data. FIG. 2 is a flow diagram showing a method 30 for biomechanical data analysis and monitoring, in accordance with one embodiment. Data is collected by and for a user (step 31). For instance, prior to a first session of the biomechanical data analysis and monitoring process, which can be accessed via an application, a user can create a profile and provide information, such as height, weight, age, sex, injury history, and profession. Other information can also be provided.

Upon login to a new movement monitoring session, additional data can be collected. For example, external data can be integrated with the user provided information, such as via an external SDK integration, which accesses data for the user from software development kit (SDK). Alternatively, or in addition, the external data can be integrated using an application programming interface (API). The external data can include, for example, sleep data, pain data, injury data, heart rate data, as well as many other types of data accessible from an external source. Environmental data, such as weather data and surface type data, can be obtained using one of or a combination of external integration or user provided input. The data provided by the user for the user's profile can also be updated, such as including or changing a status of an injury or an injury type. In addition to the user provided data, external data and environmental data, movement data can be collected for the user from one or more consumer wearable devices associated with the user.

Movement data can also be collected and associated with the user provided data, external data, and environmental data. Consumer wearable devices can collect the movement data from the individual user and can include smart headphones, such as Apple Airpods, smartphones, hearing aids, and smart wrist devices, such as a watch, as well as other types of mobile and consumer wearable devices. The data collected from the consumer wearable devices can include time, accelerometer and gyroscope data as IMU data, GPS data, altimeter data, barometer data, and movement dimensions, such as pitch, yaw and roll. Other types of data are possible.

Upon collection, the movement data is processed (step 32). The processing stage can include multiple steps: preprocessing, enrichment, and finalization. During the preprocessing phase, the data is cleaned and normalized between different sources, such as from different consumer wearable devices and users. During the enrichment phase, external and environmental data is added to the movement data collected for the user. The environmental data can include weather data, such as temperature, humidity and precipitation, and surface type data, such as paved, paving type, trail, trail type, dirt, sand, gravel, grass, or other surface types. "Trail" can identify the surface type on which the movement activity occurred, while "trail type" can identify a type of trail, such as desert, rain forest or other types.

The external data can include product specifications, such as shoe type, material composition and tread; biometric data, such as height, weight, age and gender; health history, such as injury history and pathologies; and personal activity data, such as sport and activity level. Other types of external data are possible. Each GPS point from the collected data can be enriched with the environmental, acceleration, gyroscope, altimeter, and barometer data. Also, the movement data can be aligned with the environmental and external data by day and time, or other factors.

During processing, the movement data can also be processed without the external and environmental data to determine parameters associated with the user. For example, the GPS data can be used in a route algorithm to determine a type of travel for a user, such as commuting to work, vacationing, or going to a grocery store. The GPS can also be used to identify a location of a user for determining weather at the location and surface type of the surface on which the user is travelling. Additionally, the time, acceleration, angular velocity/rotation, and attitude, such as pitch, yaw and roll, data can be used in a static balance algorithm to determine a balance score for the user, such as at a particular location or on a particular surface. The balance score can focus only on balance itself using a specific balance test, while a different balance score can be calculated later, which focuses on balance during a mixed activity session, such as one that includes standing and walking, which is further discussed below.

After the enrichment stage, the user provided, environmental, external, and movement data can be provided for additional analysis, together, to identify other factors related to movement of the user and to generate a motion template, which represents a movement fingerprint of the individual that varies by type of activity, such as walking or running and terrain type using a power spectra profile. A power spectra profile is generated for each individual for which movement data was received and is based on acceleration and gyroscope data. The power spectra profile is a personal movement fingerprint that provides how the associated individual moves in space and is further described below in detail with respect to FIG. 3. The power spectra generated by the FFT forms a movement template for the individual user. Specifically, the FFT decomposition is used to produce feature power vectors. The motion template includes these vectors.

The movement fingerprint includes information on movement mechanics, or gait mechanics, such as stability, balance, consistency, rhythm, smoothness and trends over time. For example, the balance of a user is decreasing, which could be an indicator of injury or a health issue, or stability is increasing, which can indicate recovery from an injury. The determination of other parameters using the data can include a value for distance travelled based on biomechanics metrics, such as step count, cadence, velocity, walk ratio, step length, step timing, and bounce. A delta elevation can also be determined using the data, including whether the user is moving uphill or downhill.

The fast Fourier transform (FFT) is also run on raw signals to identify parameters, such as for fitting frequency domain models. The fast Fourier transform can identify sum of sinusoids parameters and stellar oscillation parameters. Specifically, raw signals for the inertial measurement unit, such as acceleration and gyroscope data, is collected and decomposed into a sum of sinusoids through the FFT. Parameters describing the decomposed signal, for example spectral peak locations in frequency space and associated amplitudes, are extracted from the FFT.

The frequency domain models, which are designed to characterize stellar oscillations, are repurposed to instead characterize oscillations of the human body. The parameters calculated from the frequency analysis quantify characteristics of the oscillation, such as oscillation consistency, signal noise, and peak power.

Subsequently, the parameter data is finalized by engineering features and labelling the data, during which raw IMU data can be linked with other information collected at the same time, including the environmental and external data, and movement type can be identified. For example, the parameters determined using the fast Fourier transform can then be used to label sets of all the data by activity type, such as walk, run, stand, or other types of activity. The sets of data can be based on a location, time period, or other metric.

The movement data, external data, environmental data, power spectra profiles, and movement templates can be used to identify an injury and determine a walk score, as well as generate and train (step 33) AI models. Upon receipt of new data, the AI models can be rebuilt with the new data, labels, and scores.

With respect to identifying an injury, an injury status can be determined based on the score, based on trends in the values of the parameters described above, or based on patterns of correlation identified through the model. Generally, before a first movement session is initiated by a user, there is an initial training period where the model learns the individual's normal baseline of movement and range of variation. The model will continue to retrain after this training period, as the dataset grows and evolves as the individual uses their headphones, hearing aids, watch or other mobile device. Once the baseline has been established, the model will then determine "normal" and relative "outlier" activities on an individual basis. With every new activity added to the model, the importance of the activity is ranked and values of the parameters with the most importance in the model are compared to the baseline value of those parameters. By comparing the values of the top-ranked parameters for an individual between their normal and outlier bouts, we can quantify the individual's movement robustly with more degrees of sensitivity than existing models utilizing wearables data, which can then be evaluated against future activities, revealing the impact of injuries or interventions on the individual. This personal baseline also serves as a reference point for biomarkers indicating an degradation in health.

The walk score can be determined using a combination of parameters derived from the FFT, motion template and frequency domain models. The walk score provides an understandable distillation of these metrics that consumers can use to monitor their gait and movement health.

After training of the AI models, the further collected data or new data of the users can be fed (step 34) to the models for obtaining health and behavior results. The results can be provided and displayed to the individual (step 35) or used for business intelligence, and can include trends over time for the individual, predictions for movement as the individual ages or as she interacts with different environments, health monitoring, such as biomarkers of musculoskeletal and neurological health, and projected timelines for injury recovery. In one example, the user is displaying trends in her movement patterns and gait parameters that signal degradation in walk quality, such as stumbles, freezing and asymmetry, the user can be notified that a biomarker of neurological pathology has been identified.

The results for the individual can be compared (step 36) with other individuals, such as with similar age or life style, to identify a status of the individual with respect to the other individuals. Additionally, or in lieu of, the results can be compared with a population of individuals to see if the individual user is associated with the population, which can be helpful to assist in prediction of injury. For example, if the user is related to a population of users that share many characteristics, such as age, life style, and body fat percentage, and many in the population have experienced a common medical condition, the user may be notified that the medical condition is possible.

Figure 3:
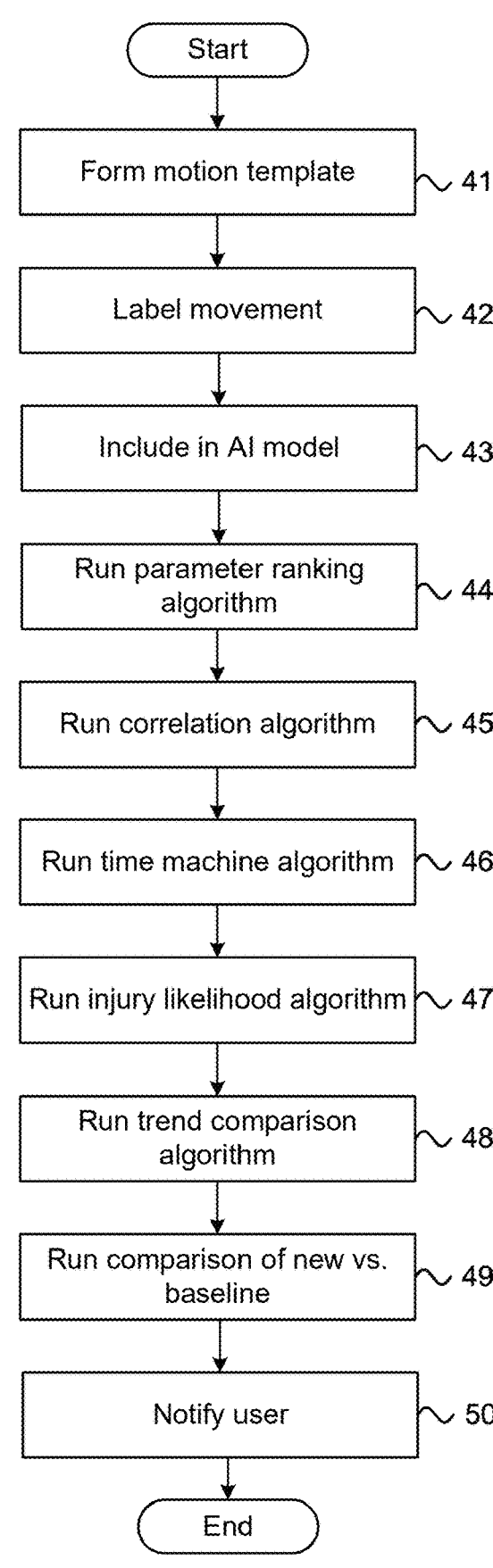
FIG. 3 is a flow diagram showing, by way of example, a data processing flow.

The power spectra profile generated for each individual is correlated with the external and environmental data and used to result in detailed movement information for the user, including variations in the user's movement patterns based on one or more factors. FIG. 3 is a flow diagram showing, by way of example, a data processing flow 40. As described above, users input data, such as biometrics and demographics, as well as injury history and current pain or illness, among other factors. Movement data for the users, such as raw acceleration, raw gyroscope, pitch/yaw/roll, GPS, and altimeter, can be collected from consumer wearables worn by the user, including headphones, phones, and watches. The GPS and altimeter data can be used to identify a habitual activity, such as walking to work or daily runs. Further, the GPS data is associated with external and environmental data, including weather, surface type, elevation, and distance.

The acceleration and gyroscope data can be used to generate a power spectra profile for each user for whom data is collected. The power spectra profile includes peak power metrics, which represents quantitative measurements, such as gait mechanics, health, footwear, apparel, and activity, as well as other types of measurements, a power spectral density, and a motion template. The quantitative measurements of the power spectra can aid in identification of an individual for whom the measurements were collected. The power spectral density is a derivative metric from the power spectra profile that allows quantitative comparisons between different spectra, and the motion template represents a movement fingerprint of the individual that varies by type of activity, such as walking or running and terrain type, or injury status. Each motion template is specific to a particular individual and new movements by the individual are compared with past movements of the individual.

The motion template can be generated (step 41) using Signal Fourier Decomposition, gait cycle detection and normalization, and feature power vectorization. A motion template is formed using feature vectors and subsequently compared with an existing motion template. Specifically, the motion template is in matrix form and new motion templates that are generated over time can be added to the matrix of the original motion template.

Movement of the user can be labeled (step 42) by activity type using the motion template. Specifically, the data associated with the movement is paired with the activity type label. The data and label are provided to the AI model, the large movement model, for that user and is analyzed by running the data though one or more algorithms, including a parameter ranking algorithm (step 44), a correlation algorithm (step 45), a time machine algorithm (step 46), an injury likelihood algorithm (step 47), a trend comparison algorithm (step 48), and a comparison of new vs baseline data algorithm (step 49). The data can be run through the algorithms one-by-one or simultaneously. Specifically, the AI model can take in the gait parameters, parameters from the FFT, motion template, frequency domain model, environmental data, user-entered data and external data. Results of the algorithms can provide scores, such as walk scores and balance score, values of some of the parameters, and labels for one or more parameters, including items of data related to movement of the user. A mixed activity static balance algorithm can optionally be performed to determine balance of a user across multiple activities, such as walking or running. In particular, one or more of the movement data, external data, environmental data, power spectra, and movement template can be used to determine the balance score across activities.

Figure 4:
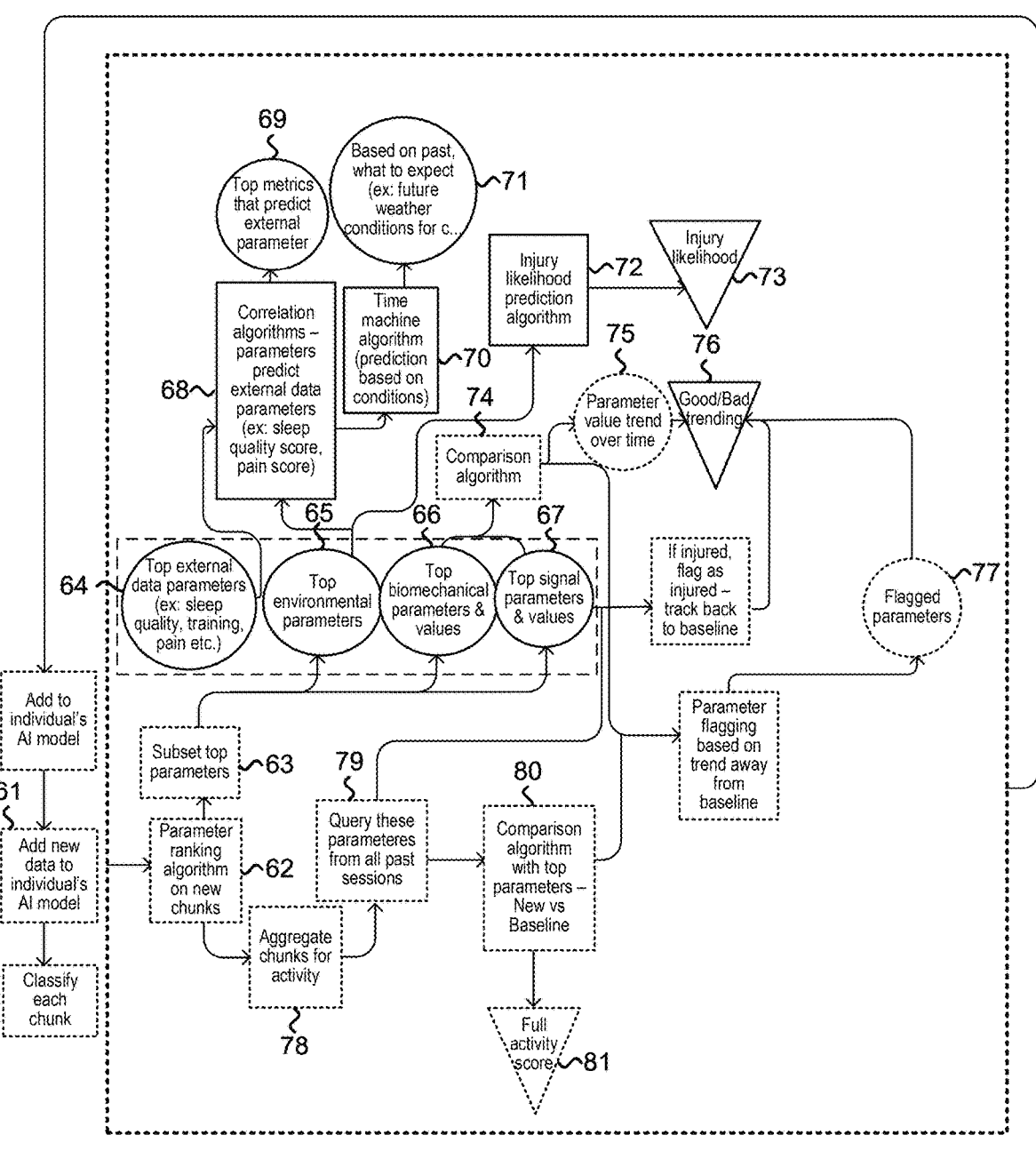
FIG. 4 is a flow diagram showing, by way of example, a flow chart for analysis of new data obtained for a user using the data process flow of FIG. 3.

FIG. 4 is a flow diagram showing, by way of example, a method 60 for analysis of new data obtained for a user via an individualized large movement model described in the data process flow of FIG. 3. As described above, new data collected for a user during a movement session, such as a run or hike, is processed 61 to determine new parameters for the user associated with that movement session, such as values for health metrics, injury predictions, and trend comparisons. In one embodiment, the newly collected data is processed 61 using an individual-level large movement model.

The new data is run through a parameter ranking algorithm 62 to rank parameters of the data collected. Top external 64, environmental 65, biomechanical 66, and signal 67 parameters are identified 63 from the new data and ran through the correlation algorithm 68, which can predict external data parameters 69. The parameters of the collected data are also run through the time machine algorithm 70 to identify "what to expect, based on the past 71," an injury likelihood predication algorithm 72 to determine a score 73 for likelihood of an injury to the user, and a comparison algorithm 74 to determine a trend 75 of a parameter value over time and whether the trend is good or bad 76. The user can be notified 77 of any trend, whether good or bad, as well as any predication of injury so that the user has the opportunity to make changes to correct the trend or prevent the injury. For instance, over time, tracking values for parameters can identify trends based on which predictions can be made. In one example, a user is walking her dog on a rainy day, and may be notified that her balance may be bad so she should exercise more than normal caution.

In one example, using the trend comparison algorithm, power spectral similarity comparisons are performed to identify a match between feature or parameter vector data to help build a "normal" baseline for the individual. The comparison should be run every time a new activity, such as logging new data by the user, is identified. Based on the spectral similarity, a movement type of the activity or session is identified. The movement type can include running, walking, biking, skating, or other movement types. The spectra can also be correlated with other components, such as activity type, including a walk to work versus walk to gym, location, environmental conditions 59 and biomechanical metrics, that can be identified once enough data is collected.

The power spectra profile correlations with activity type, location, environmental conditions and biomechanical metrics provide information regarding how the movement fingerprint of the individual varies based on factors, such as day of week, location, surface type, weather, velocity, reported pain or injury and over time. Correlations of how the fingerprint varies can be displayed to the user, along with the biomechanical metrics and reporting history of the user. The reporting history can include a discrete session log, pain chart, injury history, chronic issue tracking, and a session log with environmental conditions or product type, such as specific footwear or apparel worn by the user.

Instead of utilizing only the top ranked parameters of the new data, the new data can be ranked 62 and aggregated 78 for each activity. Subsequently, parameters of the new data aggregates are queried 79 for past sessions. A comparison algorithm 80 can compare new versus baseline data to obtain a full activity score 81. The activity score provides the user with values describing their movement and trends up or down in metrics, such as stability, balance, consistency, rhythm, and smoothness, as well as other metrics. The walk score is walking specific, whereas the activity score can be determined across other activities, for example, if the user goes for a run, there is likely a walking component and standing component, such as during warm up and cool down. The activity score breaks down the activities into their own separate components.

The resulting data of the large movement model, such as the likelihood of injury, full activity score, predictions and comparisons, provides detailed information to a user that is not readily available using conventional methods of collecting and analyzing movement data. For instance, an individual that runs every Monday for 3 miles, may clock close to 22 minutes for the run, but on a couple of Mondays clocks 23.5-25 minutes for the same 3 miles ran. Without detailed information, the user may not understand why on some Mondays the run is slower. However, correlating the power spectra profile of the individual with external and environmental data, the individual is informed that all runs with longer times are also during a particular weather condition, on a particular running surface, such as pavement, during an injury noted by the individual, or while using different products, such as footwear or apparel.

The resulting data of the large movement model can also be used to predict activity metrics or performance, predict future health, or predict health outcomes, such as injury or rehabilitation for the user. For example, metrics obtained while the user is wearing a particular pair of shoes while running on a trail can be used to predict an injury based on the particular support or lack of support provided by the shoes on an uneven running surface.

Biomechanical metrics are determined based on the raw data and the power spectra data, including acceleration and gyroscope data, and can be displayed for the user. The metrics can include peak or trough magnitudes, step count, consistency, such as timing, cadence, velocity, pace, stride length, asymmetry, and stride ration.

In addition to providing users with their own resulting data, the data can be used by many industries, such as for product testing of footwear and other athletic gear. For example, a particular pair of shoes can be tested by a user and the resulting metrics may show that the user experienced pain after four days and activity by the user decreased on days that the new shoes were worn. Alternatively, or in addition to the pain, the resulting metric may show that the shoe product impacted the user's performance or the product degraded under certain conditions. In the fitness and wellness industries, the resulting correlation data can be used to provide advanced information about the user outside of active sessions in an application, such as Nike Training Club. Further, the correlation data can be used to help identify and monitor mental health issues. For example, movement generally decreases during depressive episodes.

The user's power spectra, or "fingerprint," can be used in the identification of that user wearing the device. Once the user is identified, the power spectra correlations can be used in the health industry to provide balance data for use in concussion protocols, to monitor the effects of aging, to track cyclic changes in health, such as correlations between movement patterns and hormone changes in the female health space, as well as flare-ups in chronic pain, and determine physical therapy or rehabilitation recovery. Additionally, with respect to the medical industry, such as patient examinations in an office or using a medical platform, including a dashboard or mobile application, deviations from a user's personal baseline profile can be identified to help with diagnosis of a health condition.

Additionally, the resulting data can be used on a population-based level to predict injury, identify best conditions for a particular activity, or best locations for certain activities using machine learning or artificial intelligence models trained on aggregated data, for example, generative AI models or predictive AI models. Generalized population dynamics, such as changes in movement behavior based on season, time, or temperature, can also be monitored and predicted for a generalized population.

While the invention has been particularly shown and described as referenced to the embodiments thereof, those skilled in the art will understand that the foregoing and other changes in form and detail may be made therein without departing from the spirit and scope of the invention.

What is claimed is:

1. A method for biomechanical data analysis and monitoring, comprising:
   obtaining movement data from one or more wearable devices associated with a user;
   adding environmental data comprising outdoor conditions in which the movement data is obtained to the movement data by correlating the environmental data with specific points of the movement data;
   building a power spectral profile for the user based on the movement data and environmental data, wherein the power spectral profile comprises one or more movement profiles, which vary based on different activities performed by the user, and peak power metrics, which each represent qualitative measurements;
   correlating the power spectra with data reported by the user; and
   providing variations of the power spectral profile based on the environmental factors.

2. A method according to claim 1, further comprising:
   correlating the movement data and the environment data with external data from one or more third parties.

3. A method according to claim 1, further comprising:
   training an AI model for the user using data collected for the user comprising one or more of user provided data, external data, the environmental data, and the movement data collected from one or more mobile devices associated with the user.

4. A method according to claim 3, further comprising:
   obtaining the external data from one or more third parties via an application programming interface or a software development kit.

5. A method according to claim 3, wherein the one or more mobile devices each comprise one of a phone, laptop, tablet, smart headphones, health monitor, and smart glasses.

6. A method according to claim 1, further comprising:
   labelling segments of the movement data with an activity type.

7. A method according to claim 1, wherein the movement data comprises one or more of time, acceleration, angular velocity/rotation, attitude, altitude, elevation and global positioning satellite data.

8. A method according to claim 1, further comprising:
   utilizing the power spectra profile to make a prediction of injury; and
   notifying the user based on the prediction.

9. A method according to claim 8, further comprising:
   calculating a value for the prediction of injury to the user based on the power spectral profile.

10. A method according to claim 1, wherein the power spectra varies by day of week, location, surface type, weather, velocity, pain or injury, and over time.

\* \* \* \* \*